United States Patent [19]

Delaney

[11] 4,182,332
[45] Jan. 8, 1980

[54] RECTAL CATHETER

[76] Inventor: Richard P. Delaney, 4323 Havard St., Silver Spring, Md. 20906

[21] Appl. No.: 878,726

[22] Filed: Feb. 17, 1978

[51] Int. Cl.² .............................................. A61F 5/44
[52] U.S. Cl. .................................. 128/283; 128/349 R
[58] Field of Search .............. 128/242, 243, 244, 248, 128/251, 270, 271, 283, 286, 345, 341

[56] References Cited

U.S. PATENT DOCUMENTS

| | | | |
|---|---|---|---|
| 2,024,301 | 12/1935 | Norwood | 128/283 |
| 2,442,573 | 6/1948 | Stafford | 128/345 |
| 2,541,691 | 2/1951 | Eicher | 128/345 |
| 3,199,512 | 8/1965 | Cavanaugh et al. | 128/345 |
| 3,548,828 | 12/1970 | Vasile | 128/283 |
| 3,667,465 | 6/1972 | Voss | 128/271 |
| 3,765,413 | 10/1973 | Lepar | 128/283 |
| 3,826,242 | 7/1974 | Eggers | 128/341 |

Primary Examiner—Robert W. Michell
Assistant Examiner—C. F. Rosenbaum
Attorney, Agent, or Firm—Berman, Aisenberg & Platt

[57] ABSTRACT

An inexpensive, disposable rectal catheter which safely, gently and securely anchors the neck of a plastic bag within the patient's rectum. The device is of such simple construction that it may be both inserted and removed by the patient with one hand. The device features a stool-collecting bag having a narrow neck opening which is folded about a retaining member in the form of a cannula having a plurality of flexible, outwardly biased flanges which act to securely hold the neck of the bag against the inner wall of the rectum. To insert the retainer, an obturator is coupled to the tips of the flanges to hold same inwardly during insertion into the patient's rectum. The obturator is then removed, leaving the bag and retainer in place, which may be easily withdrawn after completion of a bowel movement by the patient.

12 Claims, 7 Drawing Figures

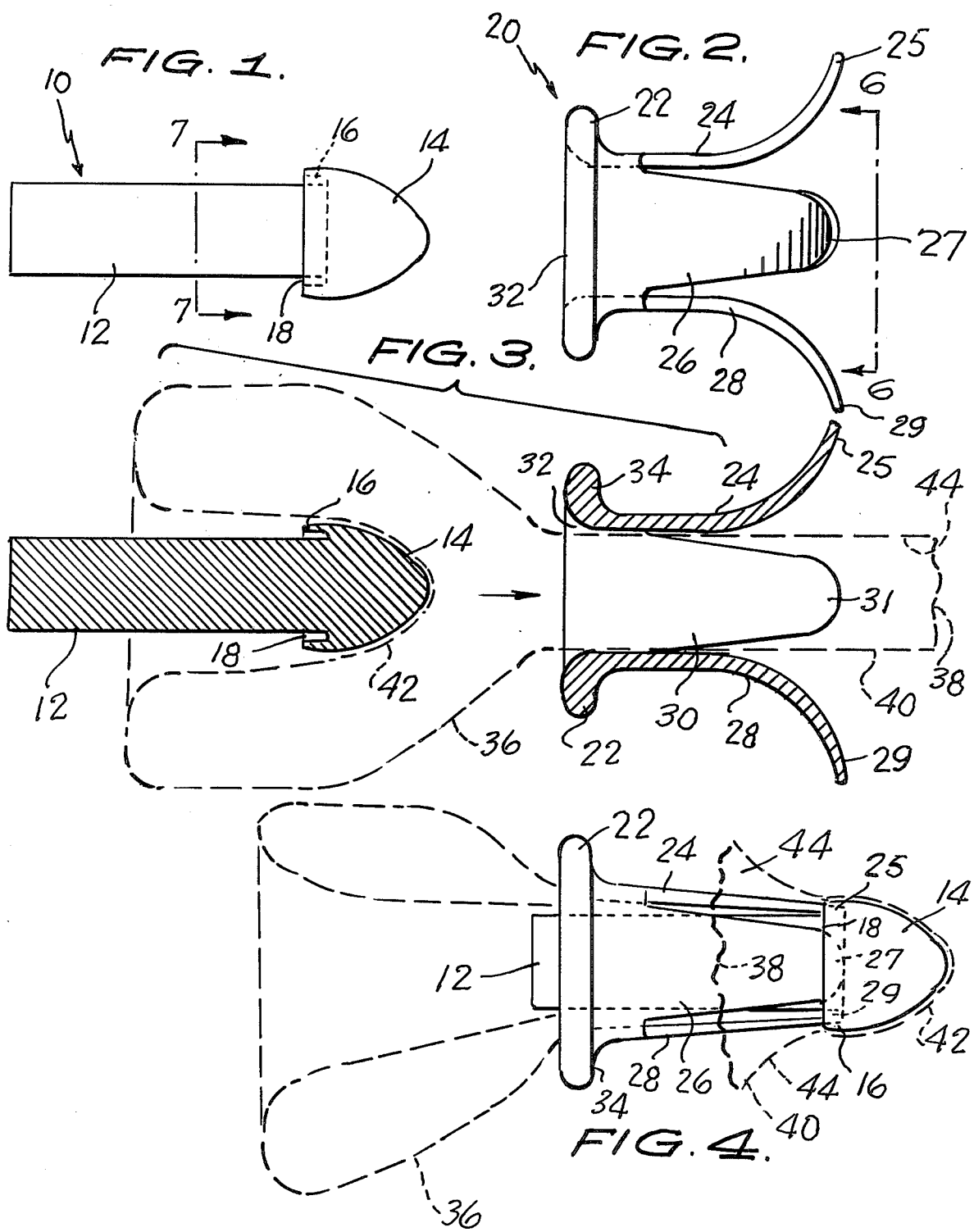

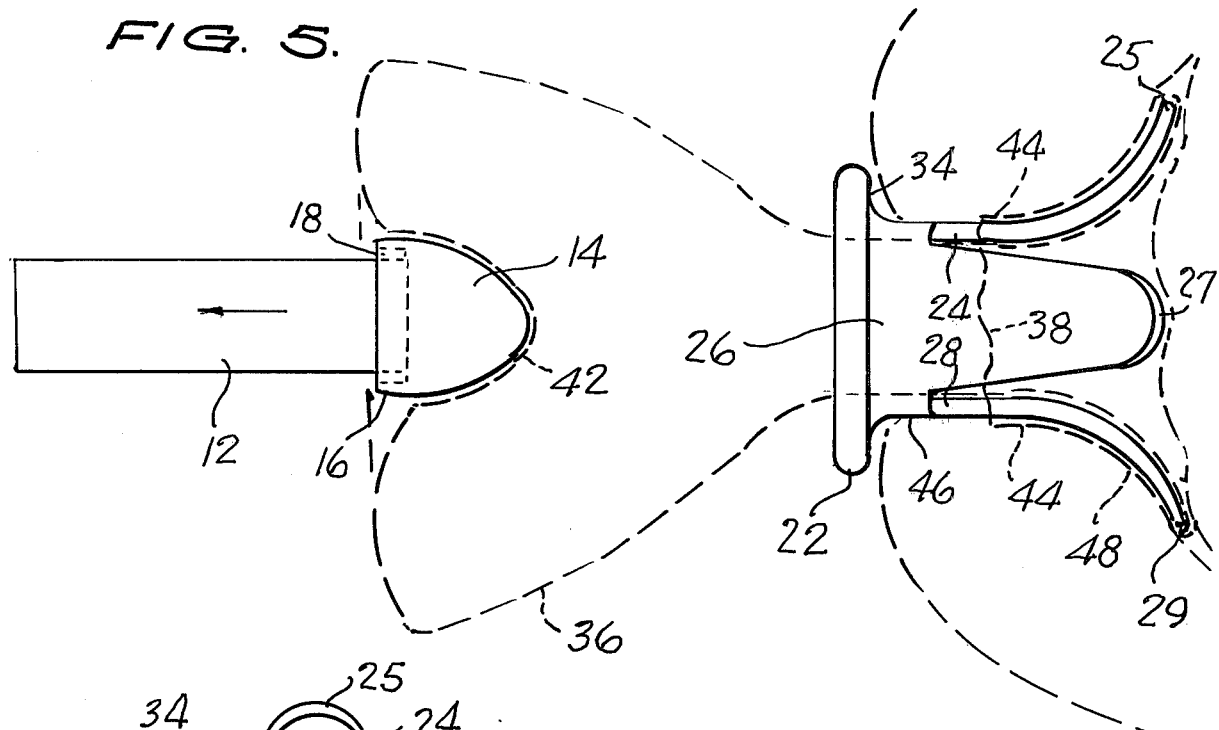
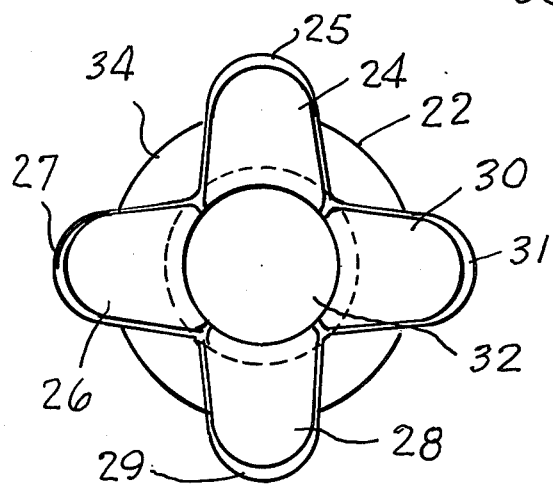
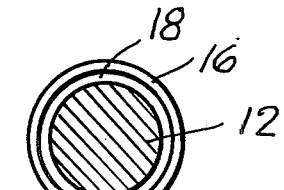

RECTAL CATHETER

BACKGROUND OF THE INVENTION

1. Field of the Invention

The present invention is related to devices for collecting stools or fecal matter from an infirm, ill or elderly patient, and, more particularly, is directed towards a rectal catheter which is inexpensive, disposable, and may be utilized by the patient in complete safety with minimum discomfort and maximum protection.

2. Description of the Prior Art

For the severely or terminally ill patient, the process involved in a bowel movement frequently becomes fraught with complications, frustration and pain. The most commonly utilized portable toilet consists of the ordinary bed pan. Bed pans, however, sometimes require the patient to assume what might be for him a very uncomfortable position, which can render the entire process difficult, if not impossible. Loose or runny stools can create not only a difficult sanitation problem, but an odor problem as well, thereby potentially causing a great deal of embarrassment and/or pain to the patient.

Several devices have been suggested by previous workers in the field which attempt to overcome some of the many disadvantages pointed out above with respect to the common bed pan. Such devices are described, for example, in U.S. Pat. Nos. 3,802,418 and 4,030,500.

The initially-cited patent to Clayton (U.S. Pat. No. 3,802,418) teaches a colon catheter which employs a hollow tube that is inserted into the anal canal and is held therein by a balloon which is inflatable via a lumen. I find this structure to be unnecessarily complex, and relatively difficult to operate, since it requires at least two hands to install and remove.

The second-cited patent to Ronnquist (U.S. Pat. No. 4,030,500) teaches a fecal matter collector which utilizes an O-ring assembly that is secured within the rectum and extends through the anal outlet of the patient. A bag is connected to the O-ring assembly externally of the anus for receiving the stool. This structure suffers from the basic deficiency, also present in the Clayton structure, that a joint is required between the collecting bag and the member retained within the rectum. The mere existence of such a joint gives rise to the possibility of a rupture or disconnection which, naturally, would be quite undesirable.

It therefore may be appreciated that it would be extremely advantageous if an economical, safe and easy to use device could be provided which minimizes the possibility of such separation, rupture or discontinuity by anchoring the neck of the actual stool-collecting bag within the anus. It would also be extremely advantageous if such a device could be easily and safely utilized by the patient himself, preferably with one hand, so as to obviate the necessity for a nurse or other assistant during insertion and removal.

I am also aware of the following United States patent which may have a bearing upon the present invention: Gunning U.S. Pat. No. 540,835.

OBJECTS AND SUMMARY OF THE INVENTION

It is therefore a primary object of the present invention to provide a new and improved rectal catheter which overcomes all of the disadvantages noted above with respect to prior art devices and techniques for collecting stools.

Another object of the present invention is to provide a rectal catheter which is inexpensive and disposable so as to be within the economic reach of any patient who requires such a device.

An additional object of the present invention is to provide a rectal catheter which will safely, gently and securely anchor the neck of a plastic bag within the rectum of a patient.

A still further object of the present invention is to provide an inexpensive and disposable rectal catheter which may be easily installed and removed by the patient himself, without outside assistance, and which may be accomplished, if necessary, with the use of only one hand.

A still further object of the present invention is to provide a unique rectal catheter which consists of only three non-integral parts which cooperate in such a fashion so as to ensure easy insertion and retention of a stool-collecting bag within the rectum for as long as may be necessary, and which permits simple and straightforward removal thereof after a bowel movement.

The foregoing and other objects are attained in accordance with one aspect of the present invention through the provision of a rectal catheter which comprises bag means for collecting fecal matter comprising a continuous flexible material having an open end defined by a neck portion, flexible means for retaining the neck portion of the bag means within the rectal opening of a patient, and obturator means selectively coupled to the bag means and the flexible means for permitting insertion thereof into the rectal opening of the patient.

In accordance with more specific objects of the present invention, the flexible means comprises a cannula including a plurality of forwardly and outwardly projecting flexibly resilient flanges. The flanges are adapted to exert pressure on the inner wall of the rectum when inserted therein. Each of the flanges includes a tip, the neck portion of the bag means being folded over the tips of the flanges so as to be retained against the inner wall of the rectum.

Even more particularly, the cannula includes a base member from which the plurality of flanges extend and which defines a central opening within which the neck portion of the bag means extends.

In accordance with other more specific aspects of the present invention, the diameter of the base member is sufficient to accommodate insertion of the obturator means therethrough, while the obturator means comprises an elongated stem portion and a forwardly positioned tip portion which includes means for retaining the tips of the flanges of the cannula against outward protrustion thereof. The means for retaining the tips comprises an annular opening formed between a rearwardly extending peripheral flange of the tip portion and the stem portion of the obturator. The obturator means is more particularly adapted to push the rear portion of the bag means through the base member to a forward position where the annular opening aligns with the tips of the flanges.

In accordance with another aspect of the present invention, a method is provided for installing a bag in the rectum to collect fecal matter of a patient, which comprises the steps of placing the neck portion of the bag through a retention member having forwardly extending and outwardly biased flexible flanges, folding the ends of the neck portion of the bag back over the tips of the flanges, attaching an insertion tool to the retention member to hold the outwardly biased flanges inwardly, inserting the forward portion of the retention member into the rectal opening of the patient, and removing the insertion tool leaving the bag and retention member in the rectum of the patient. More particularly, the step of attaching an insertion tool includes the steps of placing the insertion tool on a rear portion of the outside of the bag, pushing the rear portion of the bag forwardly with the tool through an opening formed in the rear of the retention member until the rear portion of the bag protrudes beyond the tips of the flanges, and bending the outwardly biased flanges inwardly and retaining them by means formed on the tool. Even more particularly, the step of retaining the flanges comprises the step of placing the tips of the flanges in an annular chamber formed about the periphery of the tool. The step of removing the insertion tool more particularly includes the steps of pushing the tool forwardly until the tips of the flanges of the retention member are free of the annular chamber and are biased outwardly against the inner wall of the rectum, and then pulling the tool rearwardly to be removed from the rectum.

BRIEF DESCRIPTION OF THE DRAWINGS

Various objects, aspects, features and attendant advantages of the present invention will be more fully appreciated as the same becomes better understood from the following detailed description of the present invention when considered in connection with the accompanying drawings, in which:

FIG. 1 is a side view which illustrates one of the three basic components which together comprise a preferred embodiment of the present invention;

FIG. 2 is a side view of a second component which comprises a portion of the preferred embodiment of the present invention;

FIG. 3 is a side sectional view which illustrates all three of the components which together comprise a preferred embodiment of the present invention and which illustrates an initial installation stage;

FIG. 4 is a side view similar to that of FIG. 3 but which illustrates a subsequent installation step;

FIG. 5 is a view similar to FIG. 4 but which illustrates the preferred embodiment of the present invention after retention in the rectum of the patient has been achieved;

FIG. 6 is an end view of the element illustrated in FIG. 2 and taken along line 6—6 thereof; and FIG. 7 is a cross-sectional view of the element illustrated in FIG. 1 and taken along line 7—7 thereof.

DETAILED DESCRIPTION OF THE PREFERRED EMBODIMENTS

Referring now to the drawings, wherein like reference numerals represent identical or corresponding parts throughout the several views, and more particularly to FIG. 1 thereof, reference numeral 10 indicates generally an insertion tool or obturator which forms one of the three basic components which together comprise the preferred embodiment of the present invention. The obturator 10 comprises an elongated, preferably plastic, generally cylindrical stem or body portion 12 which terminates at its forward end in an enlarged tip portion 14 which tapers as illustrated to a forwardly projecting point. The specific size and shape of tip 14 are selected so as to facilitate insertion thereof into the rectal opening of the patient, as will become more clear hereinafter.

The outer periphery of the tip portion 14 extends rearwardly past its point of attachment with the stem 12 to form a flange 16 which is spaced from the stem 12 so as to define an annular recess 18. Recess 18 extends about the entire periphery of stem 12 (see FIG. 7), for a purpose which will be described in greater detail hereinafter.

Referring now to FIGS. 2 and 6, there is illustrated in side and end views, respectively, a bag retention member or cannula which is indicated generally by reference numeral 20 and which forms the second component of the three basic components which together comprise a preferred embodiment of the present invention.

The cannula 20 includes a substantially rigid, ring-shaped base member 22 which is adapted, during use, to be positioned externally of and adjacent the patient's rectum.

Extending laterally from the base member 22 are a plurality of resiliently flexible retaining flanges 24, 26, 28 and 30. Although four of such retaining flanges are illustrated, it is clear that greater or fewer may be utilized within the spirit and scope of the present invention.

The flanges 24, 26, 28 and 30 each have tip portions 25, 27, 29 and 31, respectively, and are each equi-distantly spaced about the periphery of base member 22.

The cannula 20 is preferably formed of plastic, and the flanges 24, 26, 28 and 30 are molded or formed by any suitable technique so as to be normally biased outwardly as illustrated in their quiescent state in FIGS. 2 and 6.

Flanges 24 through 30 define a central opening 32 which is sufficiently dimensioned to accommodate the largest outer diameter of the obturator 10, for reasons which will become more clear hereinafter. Further, the base member 22 includes a substantially flat inner surface 34 which serves as a means for retaining same externally of the rectum, to be described in more detail below.

Referring now to FIG. 3, the third component of the preferred embodiment of the present invention is illustrated as comprising a bag 36 which is preferably integrally and continuously formed, without seams, of a flexible material, such as plastic, so as to be economically available and readily disposable. The bag 36 includes a forwardly positioned open end 38 which is defined by a neck portion 40. Reference numeral 42 indicates a rear portion of the bag 36 initially engaged by the obturator 10, in a manner to be described below.

In operation, the neck portion 40 of the bag 36 is initially placed through the central opening 32 of cannula 20 so that the open end 38 is approximately at the position shown in FIG. 3. The tip 14 of the obturator or insertion tool 10 is then positioned as illustrated in FIG. 3 so as to push rear portion 42 of bag 36 forwardly, through the central opening 32, past the tips 25, 27, 29 and 31 of the flanges 24 through 30.

The portion of the neck 40 of bag 36 adjacent the open end 38 is folded back over the tips 25, 27, 29 and 31 such that the inside surface 44 of the neck 40 becomes the exposed, outer surface of the folded bag portion thereof as illustrated in FIG. 4.

The tip portions 25, 27, 29 and 31 may then be compressed or bent inwardly, as by hand, whereupon they may then be placed within the annular recess 18 of the obturator tip 14 to hold same in the position illustrated in FIG. 4. Some care must be taken to provide sufficient bag material about the tip 14 of the obturator 10 to avoid puncturing the bag when the tips 25 through 31 are inserted in the recess 18.

The forwardly exposed portions of the bag 36, namely portions 42 and 44 in their position of FIG. 4, may then be lubricated, by means of a conventional antiseptic jelly or the like, to facilitate insertion of the forward portion of the present invention into the rectal opening 46 of the patient, as illustrated in FIG. 5.

After the forwardmost portions of obturator 10, cannula 20, and bag 36 have been inserted into the rectal opening 46 of the patient, to the position where flange 34 of base member 22 contacts the rear rectal opening, it may be appreciated that the tips 25 through 31 of the flanges 24 through 30, respectively, may be released by slightly pushing forward on the stem 12 of the obturator 10. The base 34 of ring member 22 prevents forward movement of the cannula 20, and, upon forward movement of stem 12, recess 18 releases the outwardly biased, resilient tips 25 through 31. The outward biasing of tips 25 through 31 serve to retain the folded back portion 44 of neck 40 of bag 36 against the inner wall of the rectum, known as the ampula 48.

The obturator 10 may then be easily removed by grasping stem 12 and withdrawing same outwardly through opening 32 in base member 22 to leave retaining member 20 and bag 36 in a retained position within the rectum of the patient, illustrated in FIG. 5. Removal of obturator 10 will result in the rear portion 42 of bag 36 being returned to its normal position, so that the bag is ready to receive the stool of the patient.

It should be noted that the folded back portion 44 of neck 40 of bag 36, upon which is applied lubricating jelly prior to insertion, is in contact with the inner wall of the rectum while cannula 20 is in place. The lubricant placed on portion 44 serves to keep bag 36 in close contact with the skin immediately adjacent the point where the stool is to enter bag 36, thereby providing protection from any small amount of liquid which may otherwise tend to leak out.

To remove the bag, the patient need simply grasp the base member 22 and pull gently to withdraw same from the rectum. The folded back portion 44 of the bag will essentially be clean, and serves as a means for facilitating sealing of the bag for subsequent disposal or transportion to a laboratory for analysis.

Obviously, numerous modifications and variations of the present invention are possible in light of the above teachings. For example, the size of the body of the bag may be varied to accommodate those patients which may have a problem of frequent small, runny stools, with whom the device could be utilized in an indwelling fashion. It may be necessary in this instance to have a small pinch valve on the bag which would be utilized to release flatus either into an activated charcoal gas collector or into the atmospheric air.

It is therefore to be understood that within the scope of the appended claims, the invention may be practiced otherwise than as specifically described herein.

I claim as my invention:

1. A rectal catheter, which comprises:
   bag means for collecting fecal matter comprising a continuous flexible material having an open end defined by a neck portion;
   flexible means for retaining said neck portion of said bag means within the rectal opening of a patient; said flexible means including a cannula having a plurality of forwardly and outwardly projecting flexible and resilient flanges adapted to exert pressure on the inner wall of the rectum when inserted therein, each of said flanges including a tip; and
   obturator means selectively coupled to said bag means and said flexible means for permitting insertion thereof into the rectal opening of said patient while said neck portion of said bag means is folded over the tips of said flanges so as to be retained against the inner wall of the rectum.

2. The rectal catheter as set forth in claim 1, wherein said obturator means is provided with releasable latching means for holding the tips of said flexibly resilient flanges pressed inwardly in substantial cylindrical alignment with said cannula during insertion into said rectal opening and while the rear portion of the bag means is pushed forwardly through the cannula by forward movement of the obturator means, said obturator means being movable in the cannula to a further forward position which releases said latching means allowing the resilient flanges to press the neck of the bag means outwardly against the inner wall of the rectal opening, while subsequent withdrawal of the obturator means permits emergence of the rear portion of the bag means through the cannula and out of the rectal opening.

3. The rectal catheter as set forth in claim 1, wherein said cannula further includes a base member from which said plurality of flanges extend and which defines a central opening within which said neck portion of said bag means extends.

4. The rectal catheter as set forth in claim 3, wherein the diameter of said base member is sufficient to accommodate insertion of said obturator means therethrough.

5. The rectal catheter as set forth in claim 4, wherein said obturator means comprises an elongated stem portion and a forwardly positioned tip portion including means for retaining said tips of said flanges of said cannula against outward protrusion thereof.

6. The rectal catheter as set forth in claim 5, wherein said means for retaining said tips comprises an annular opening formed between a rearwardly extending peripheral flange of said tip portion and said stem portion.

7. The rectal catheter as set forth in claim 6, wherein said obturator means is adapted to push the rear portion of said bag means through said base member to a forward position where said annular opening aligns with said tips of said flanges.

8. The rectal catheter as set forth in claim 7, wherein said obturator means is movable to a still further forward position through said base member which releases said tips from said annular opening permitting subsequent withdrawal of the obturator means from said cannula.

9. A method of installing a bag in the rectum to collect fecal matter of a patient, which comprises the steps of:
   placing the neck portion of said bag through a retention member having forwardly extending and outwardly biased flexible flanges;
   folding the end of said neck portion of said bag back over the tips of said flanges;
   attaching an insertion tool to said retention member to hold said outwardly biased flanges inwardly;
   inserting the forward portion of said retention member into the rectal opening of the patient; and
   removing the insertion tool leaving the bag and retention member in the rectum of the patient.

10. The method as set forth in claim 9, wherein said step of attaching an insertion tool includes the steps of:
placing said insertion tool on a rear portion of the outside of said bag;
pushing said rear portion of said bag forwardly with said tool through an opening formed in the rear of said retention member until said rear portion protrudes beyond the tips of said flanges; and
bending the outwardly biased flanges inwardly and retaining them by means formed on said tool.

11. The method as set forth in claim 10, wherein said step of retaining said flanges comprises the step of placing the tips of the flanges in an annular chamber formed about the periphery of said tool.

12. The method as set forth in claim 11, wherein said step of removing the insertion tool includes the steps of:
pushing said tool forwardly until the tips of the flanges of the retention member are free of the annular chamber and are biased outwardly against the inner wall of the rectum; and
then pulling said tool rearwardly from said rectum.

* * * * *